(12) United States Patent
Zhuo et al.

(10) Patent No.: US 12,430,890 B2
(45) Date of Patent: Sep. 30, 2025

(54) OBJECT DETECTION MODEL TRAINING METHOD AND APPARATUS, OBJECT DETECTION METHOD AND APPARATUS, COMPUTER DEVICE, AND STORAGE MEDIUM

(71) Applicant: TENCENT TECHNOLOGY (SHENZHEN) COMPANY LIMITED, Guangdong (CN)

(72) Inventors: Jiaxuan Zhuo, Shenzhen (CN); Hong Shang, Shenzhen (CN); Zhongqian Sun, Shenzhen (CN); Han Zheng, Shenzhen (CN); Xinghui Fu, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 879 days.

(21) Appl. No.: 17/682,353

(22) Filed: Feb. 28, 2022

(65) Prior Publication Data

US 2022/0189147 A1    Jun. 16, 2022

Related U.S. Application Data

(63) Continuation of application No. PCT/CN2020/126430, filed on Nov. 4, 2020.

(30) Foreign Application Priority Data

Feb. 13, 2020 (CN) .......................... 202010090909.6

(51) Int. Cl.
*G06V 10/25* (2022.01)
*G06F 18/214* (2023.01)
(Continued)

(52) U.S. Cl.
CPC .......... *G06V 10/774* (2022.01); *G06T 7/0012* (2013.01); *G06T 7/73* (2017.01);
(Continued)

(58) Field of Classification Search
None
See application file for complete search history.

(56) References Cited

U.S. PATENT DOCUMENTS

| | | | |
|---|---|---|---|
| 10,373,027 B1 | 8/2019 | Kim et al. | |
| 11,633,084 B2 * | 4/2023 | Hirasawa | G06T 7/0012 382/128 |
| 2019/0286940 A1 * | 9/2019 | Shen | G06T 11/60 |

FOREIGN PATENT DOCUMENTS

| | | |
|---|---|---|
| CN | 107256552 A | 10/2017 |
| CN | 108133220 A | 6/2018 |

(Continued)

OTHER PUBLICATIONS

Written Opinion for PCT/CN2020/126430, dated Feb. 5, 2021.
(Continued)

*Primary Examiner* — Mohammed Rachedine
(74) *Attorney, Agent, or Firm* — Sughrue Mion, PLLC

(57) ABSTRACT

An object detection model training method includes: inputting an unannotated first sample image into an initial detection model of a current round, and outputting a first prediction result for a target object, transforming the first sample image and a first prediction position region within the first prediction result to obtain a second sample image and a prediction transformation result in the second sample image; inputting the second sample image into the initial detection model, and outputting a second prediction result for the target object; obtaining a loss value of unsupervised learning according to a difference between the second prediction result and the prediction transformation result; and adjusting model parameters of the initial detection model according to (Continued)

the loss value and returning to the operation of inputting a first sample image into an initial detection model of a current round to perform iterative training, to obtain an object detection model.

20 Claims, 5 Drawing Sheets

(51) Int. Cl.
| | |
|---|---|
| *G06N 3/088* | (2023.01) |
| *G06T 7/00* | (2017.01) |
| *G06T 7/73* | (2017.01) |
| *G06V 10/40* | (2022.01) |
| *G06V 10/764* | (2022.01) |
| *G06V 10/774* | (2022.01) |
| *G06V 10/776* | (2022.01) |
| *G06V 10/778* | (2022.01) |
| *G06V 10/82* | (2022.01) |
| *G16H 30/40* | (2018.01) |
| *G16H 50/20* | (2018.01) |
| *G16H 50/70* | (2018.01) |
| *A61B 1/00* | (2006.01) |
| *A61B 1/31* | (2006.01) |

(52) U.S. Cl.
CPC ............ *G06V 10/40* (2022.01); *G06V 10/764* (2022.01); *G06V 10/776* (2022.01); *G06V 10/7784* (2022.01); *G16H 30/40* (2018.01); *A61B 1/000094* (2022.02); *A61B 1/000096* (2022.02); *A61B 1/31* (2013.01); *G06T 2207/20081* (2013.01); *G06T 2207/30032* (2013.01); *G06V 2201/032* (2022.01)

(56) References Cited

FOREIGN PATENT DOCUMENTS

| | | | | | |
|---|---|---|---|---|---|
| CN | 108229276 | A | | 6/2018 | |
| CN | 109426782 | A | | 3/2019 | |
| CN | 109657615 | A | | 4/2019 | |
| CN | 109697460 | A | * | 4/2019 | ........... G06F 18/214 |
| CN | 110097105 | A | * | 8/2019 | ........... G06K 9/6256 |
| CN | 110322438 | A | | 10/2019 | |
| CN | 110852285 | A | * | 2/2020 | ........... G06F 18/241 |
| CN | 111291755 | A | | 6/2020 | |
| WO | WO-2021097302 | A1 | * | 5/2021 | ........... G06K 9/6226 |

OTHER PUBLICATIONS

International Search Report for PCT/CN2020/126430, dated Feb. 5, 2021.
Sohn et al., "FixMatch: Simplifying Semi-Supervised Learning with Consistency and Confidence", URL: https://arxiv.org/pdf/2001.07685vl.pdf, Jan. 21, 2020 (14 pages total).

* cited by examiner

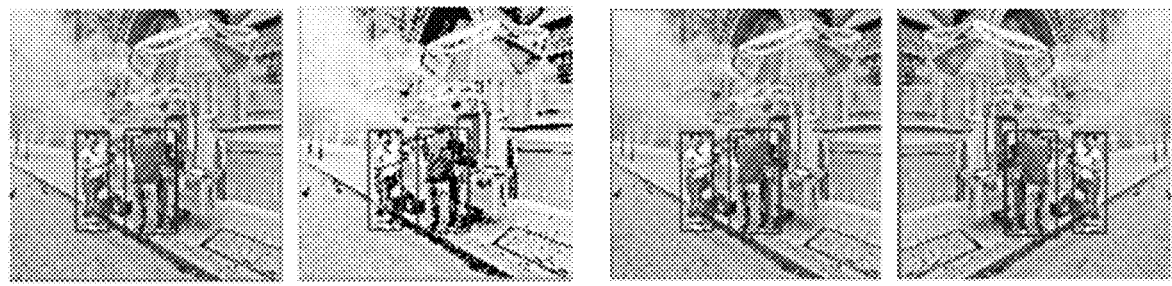
(a) Color perturbation
FIG. 3(a)
(b) Horizontal flipping
FIG. 3(b)
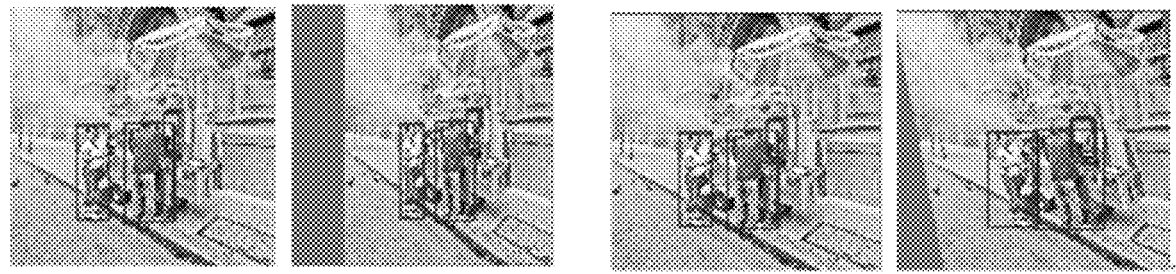
(c) Stretching and translation
FIG. 3(c)
(d) Affine change
FIG. 3(d)
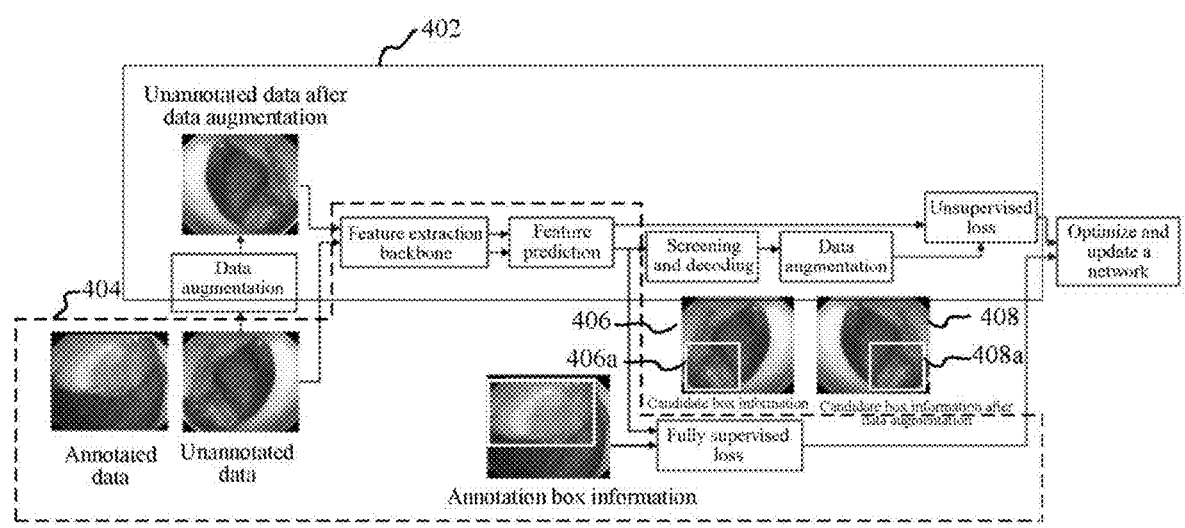
FIG. 4

OBJECT DETECTION MODEL TRAINING METHOD AND APPARATUS, OBJECT DETECTION METHOD AND APPARATUS, COMPUTER DEVICE, AND STORAGE MEDIUM

CROSS-REFERENCE TO RELATED APPLICATION(S)

This application is a continuation application of International Application No. PCT/CN2020/126430, filed on Nov. 4, 2020 which claims priority to Chinese Patent Application No. 202010090909.6, filed with the China National Intellectual Property Administration on Feb. 13, 2020, the disclosures of which are incorporated by reference in their entireties.

FIELD

The present disclosure relates to the field of artificial intelligence (AI) technologies and the field of machine learning (ML) technologies, and in particular, to an object detection model training method and apparatus, an object detection method and apparatus, a computer device, and a storage medium.

BACKGROUND

With the rapid development of science and technology, AI technologies have received increasingly more attention. Specifically, ML technology in the AI technologies is widely applied. Generally, an ML model capable of positioning and recognizing a target object may be trained by using the ML technology. For example, a medical image is used as a sample, and an object detection model is trained using the ML technology to recognize a target object in the medical image.

Supervised learning is a conventional model training method. However, a supervised learning method involves acquiring a large amount of annotated data to the sample, resulting in a relatively high cost of model training.

SUMMARY

According to embodiments provided in the disclosure, an object detection model training method and apparatus, a computer device, and a storage medium are provided. In addition, an object detection method and apparatus, a computer device, and a storage medium are further provided.

According to an aspect of the disclosure, an object detection model training method is provided, performed by a computer device, the method including: inputting a first sample image into an initial detection model of a current round and outputting a first prediction result for a target object, the first sample image not carrying position annotation information of the target object; transforming the first sample image and a first prediction position region of the target object in the first prediction result to obtain a second sample image and a prediction transformation result for the target object in the second sample image; inputting the second sample image into the initial detection model and outputting a second prediction result for the target object; obtaining a loss value of unsupervised learning according to a difference between the second prediction result and the prediction transformation result; and adjusting model parameters of the initial detection model according to the loss value, using a next round as the current round, and returning to the operation of inputting a first sample image into an initial detection model of a current round to perform iterative training, until a training end condition is met, to obtain an object detection model.

According to an aspect of the disclosure, an object detection method is provided, performed by a computer device, the method including: inputting a target image to be processed into a pre-trained object detection model, and outputting a positioning result for a target object in the target image; and the object detection model is obtained through training operations of the object detection model, and the training operations of the object detection model include: inputting a first sample image into an initial detection model of a current round, and outputting a first prediction result for a target object, the first sample image not carrying position annotation information of the target object; transforming the first sample image and a first prediction position region of the target object in the first prediction result to obtain a second sample image and a prediction transformation result for the target object in the second sample image; inputting the second sample image into the initial detection model and outputting a second prediction result for the target object; obtaining a loss value of unsupervised learning according to a difference between the second prediction result and the prediction transformation result; and adjusting model parameters of the initial detection model according to the loss value, using a next round as the current round, and returning to the operation of inputting a first sample image into an initial detection model of a current round to perform iterative training until a training end condition is met, to obtain an object detection model.

According to an aspect of the disclosure, an object detection method is provided, performed by a computer device, the method including: inputting a target colorectal polyp medical image to be processed into a pre-trained colorectal polyp detection model to predict a positioning result of a colorectal polyp; and training operations of the colorectal polyp detection model include: inputting an unannotated first colorectal polyp sample medical image into an initial detection model of a current round, and outputting a first prediction result for a colorectal polyp; transforming the first colorectal polyp sample medical image and a first prediction position region of the colorectal polyp in the first prediction result to obtain a second colorectal polyp sample medical image and a prediction transformation result for the colorectal polyp in the second colorectal polyp sample medical image; inputting the second colorectal polyp sample medical image into the initial detection model, and outputting a second prediction result for the colorectal polyp; obtaining a loss value of unsupervised learning according to a difference between the second prediction result and the prediction transformation result; and adjusting model parameters of the initial detection model according to the loss value, using a next round as the current round, and returning to the operation of inputting a first colorectal polyp sample medical image into an initial detection model of a current round to perform iterative training, until a training end condition is met, to obtain a colorectal polyp detection model.

According to an aspect of the disclosure, an object detection model training apparatus may be provided, including: a prediction module, configured to input a first sample image into an initial detection model of a current round, and output a first prediction result for a target object, the first sample image not carrying position annotation information of the target object; a transformation module, configured to transform the first sample image and a first prediction position region of the target object in the first prediction result, to obtain a second sample image and a prediction transformation result for the target object in the second sample image, the prediction module being further configured to input the second sample image into the initial detection model, and output a second prediction result for the target object; an unsupervised loss determining module, configured to obtain a loss value of unsupervised learning according to a difference between the second prediction result and the prediction transformation result; and a parameter adjustment module, configured to adjust model parameters of the initial detection model according to the loss value, notify the prediction module to use a next round as the current round, and continue to perform the operation of inputting a first sample image into an initial detection model of a current round to perform iterative training, until a training end condition is met, to obtain an object detection model.

According to an aspect of the disclosure, an object detection apparatus may be provided, including: a model training module, configured to input a first sample image into an initial detection model of a current round, and output a first prediction result for a target object, the first sample image not carrying position annotation information of the target object; transform the first sample image and a first prediction position region of the target object in the first prediction result, to obtain a second sample image and a prediction transformation result for the target object in the second sample image; input the second sample image into the initial detection model, and output a second prediction result for the target object; obtain a loss value of unsupervised learning according to a difference between the second prediction result and the prediction transformation result; and adjust model parameters of the initial detection model according to the loss value, use a next round as the current round, and return to the operation of inputting a first sample image into an initial detection model of a current round to perform iterative training, until a training end condition is met, to obtain an object detection model; and a positioning detection module, configured to input a target image to be processed into the pre-trained object detection model, and output a positioning result for a target object in the target image.

According to an aspect of the disclosure, an object detection apparatus is provided, disposed in a computer device, the apparatus including: a model training module, configured to input an unannotated first colorectal polyp sample medical image into an initial detection model of a current round, and output a first prediction result for a colorectal polyp; transform the first colorectal polyp sample medical image and a first prediction position region of the colorectal polyp in the first prediction result, to obtain a second colorectal polyp sample medical image and a prediction transformation result for the colorectal polyp in the second colorectal polyp sample medical image; input the second colorectal polyp sample medical image into the initial detection model, and output a second prediction result for the colorectal polyp; obtain a loss value of unsupervised learning according to a difference between the second prediction result and the prediction transformation result; and adjust model parameters of the initial detection model according to the loss value, use a next round as the current round, and return to the operation of inputting a first colorectal polyp sample medical image into an initial detection model of a current round to perform iterative training, until a training end condition is met, to obtain a colorectal polyp detection model; and a positioning detection module, configured to input a target colorectal polyp medical image to be processed into the pre-trained colorectal polyp detection model to predict a positioning result of a colorectal polyp in the colorectal polyp medical image.

According to an aspect of the disclosure, a computer device may be provided, including a memory and one or more processors, the memory storing computer-readable instructions, the computer-readable instructions, when executed by the one or more processors, causing the one or more processors to perform the operations in the method according to the embodiments of the disclosure.

According to an aspect of the disclosure, one or more non-transitory computer-readable storage media may be provided, storing computer-readable instructions, the computer-readable instructions, when executed by one or more processors, causing the one or more processors to perform the operations in the method according to the embodiments of the disclosure.

Details of one or more embodiments of the disclosure are provided in the following accompany drawings and descriptions. Other features, objectives, and advantages of the disclosure become more obvious based on the specification, the accompanying drawings, and the claims.

BRIEF DESCRIPTION OF THE DRAWINGS

To describe the technical solutions in embodiments of the disclosure more clearly, the following briefly introduces the accompanying drawings required for describing the embodiments. The accompanying drawings in the following description show only some embodiments of the disclosure, and a person of ordinary skill in the art may still derive other accompanying drawings from the accompanying drawings without creative efforts. In addition, one of ordinary skill would understand that aspects of example embodiments may be combined together or implemented alone.

FIG. 3(a) is a schematic diagram of data augmentation in an embodiment.

FIG. 3(b) is a schematic diagram of data augmentation in an embodiment.

FIG. 3(c) is a schematic diagram of data augmentation in an embodiment.

FIG. 3(d) is a schematic diagram of data augmentation in an embodiment.

FIG. 4 is a schematic principle diagram of an object detection model training method in an embodiment.

DESCRIPTION OF EMBODIMENTS

To make the objectives, technical solutions, and advantages of the disclosure clearer and more understandable, the disclosure is further described in detail below with reference to the accompanying drawings and the embodiments. The described embodiments are not to be construed as a limitation to the present disclosure. All other embodiments obtained by a person of ordinary skill in the art without creative efforts shall fall within the protection scope of the present disclosure.

Figure 1:
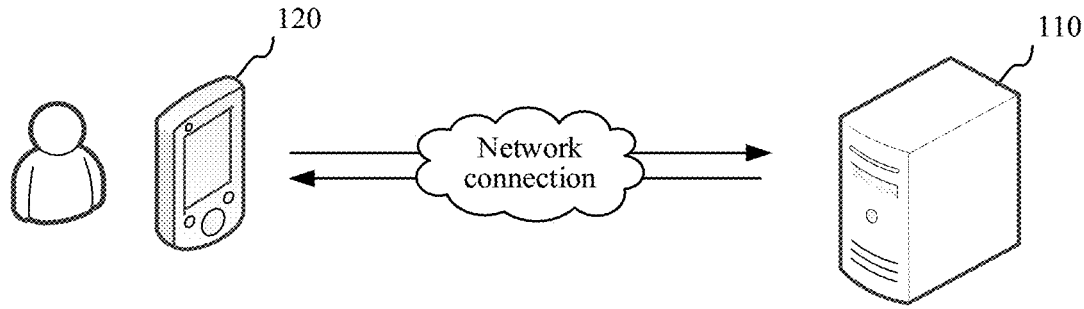
FIG. 1 is a diagram of an application scenario of an object detection model training method in an embodiment.

FIG. 1 is a diagram of an application scenario of an object detection model training method in an embodiment. Referring to FIG. 1, the application scenario includes a server 110 and a terminal 120 that are connected to a network. The terminal 120 may be a medical device, a desktop computer, or a mobile terminal. The medical device is a terminal device capable of acquiring a medical image. The mobile terminal may include at least one of a mobile phone, a tablet computer, a notebook computer, a personal digital assistant (PDA), and a wearable device. The server 110 may be implemented by using an independent server or a server cluster including a plurality of physical servers. It may be understood that in other embodiments, the server 110 may alternatively be replaced with a terminal capable of performing the object detection model training method in the embodiments of the disclosure.

The terminal 120 may acquire an image, and send the acquired image as a sample image to the server 110 to provide the sample image for model training to the server 110. For example, in a medical scenario, the medical device may acquire a medical image and provide the medical image to the server 110, and the server 110 may use the medical image as a sample image for ML training to train an object detection model capable of recognizing a target object in the medical image. It may be understood that, the server 110 may alternatively directly obtain a stored sample image sent by the terminal 120.

It may be understood that, the server 110 needs to train the object detection model through a plurality of rounds of iterations. Therefore, during each round of iterative training, the server 110 may input a first sample image into an initial detection model of a current round, and output a first prediction result for a target object, the first sample image not carrying position annotation information of the target object. That is, the first sample image is unannotated sample data. The server 110 may transform the first sample image and a first prediction position region of the target object in the first prediction result, to obtain a second sample image and a prediction transformation result for the target object in the second sample image. The server 110 may input the second sample image into the initial detection model, and output a second prediction result for the target object; obtain a loss value of unsupervised learning according to a difference between the second prediction result and the prediction transformation result; and adjust model parameters of the initial detection model according to the loss value, use a next round as the current round, and return to the operation of inputting a first sample image into an initial detection model of a current round to perform iterative training, until a training end condition is met, to obtain an object detection model.

It may be understood that, the object detection model training method in the embodiments of the disclosure is equivalent to using AI technologies to train an ML model capable of automatically positioning a target object.

AI is a theory, method, technology, and application system that uses a digital computer or a machine controlled by the digital computer to simulate, extend, and expand human intelligence, perceive an environment, obtain knowledge, and use knowledge to obtain an optimal result. In other words, the AI is a comprehensive technology of computer science, which attempts to understand essence of intelligence and produces a new intelligent machine that responds in a manner similar to human intelligence. The AI is to study design principles and implementation methods of various intelligent machines, so that the machines have the functions of perception, reasoning, and decision-making.

The AI technology is a comprehensive discipline, covering a wide range of fields including both a hardware-level technology and a software-level technology. The basic AI technology generally includes a technology such as a sensor, a dedicated AI chip, cloud computing, distributed storage, a big data processing technology, an operation/interaction system, or mechatronics. An AI software technology mainly includes fields such as a computer vision (CV) technology, a speech processing technology, a natural language processing technology, and ML/deep learning (DL).

It may be understood that, the object detection model training method in the embodiments of the disclosure is equivalent to using an ML technology. ML is a multi-field interdiscipline involving a plurality of disciplines such as probability theory, statistics, approximation theory, convex analysis, and algorithm complexity theory. The ML specializes in studying how a computer simulates or implements a human learning behavior to obtain new knowledge or skills, and reorganize an existing knowledge structure, so as to keep improving its performance. The ML is a core of the AI, is a basic way to make the computer intelligent, and is applied to various fields of the AI. The ML and DL generally include technologies such as an artificial neural network, a belief network, reinforcement learning, transfer learning, inductive learning, and imitation learning.

Figure 2:
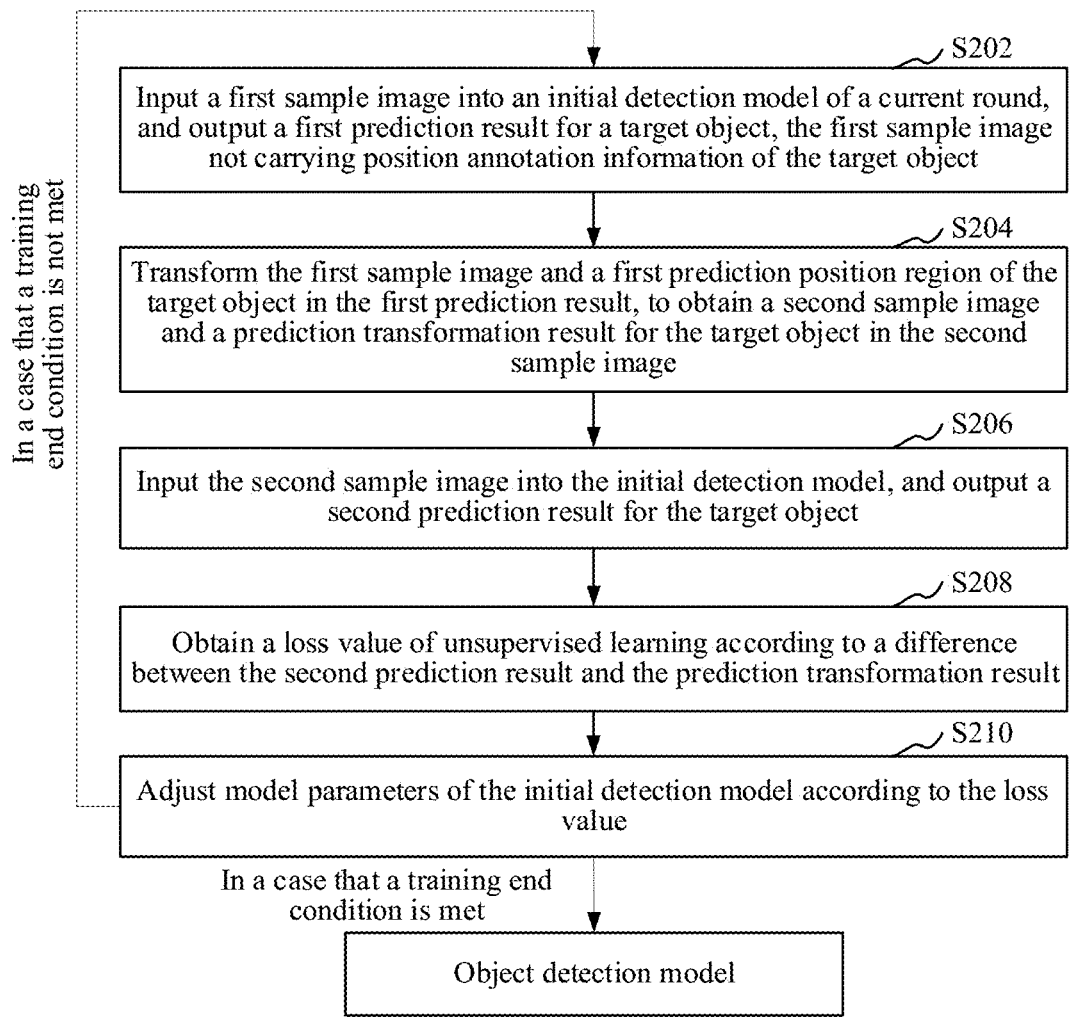
FIG. 2 is a schematic flowchart of an object detection model training method in an embodiment.

FIG. 2 is a schematic flowchart of an object detection model training method in an embodiment. The object detection model training method in this embodiment may be performed by a computer device. The computer device may be one or more devices. For example, the computer device may be a server or a terminal, or may be a combination of a server and a terminal. That is, the object detection model training method may be performed by the server, or may be implemented by the terminal and the server together. Description is mainly made currently by using an example in which the computer device is the server 110 in FIG. 1. Referring to FIG. 2, the method specifically includes the following operations:

S202. Input a first sample image into an initial detection model of a current round, and output a first prediction result for a target object, the first sample image not carrying position annotation information of the target object.

The sample image is an image used as sample data for model training. The target object is a target object that needs to be positioned and recognized. It may be understood that, the first sample image may include image content of the target object. The position annotation information is information used for annotating a position of the target object in the sample image. Because the first sample image does not carry the position annotation information of the target object, and it indicates that the first sample image is unannotated sample data, the first sample image being used for model training belongs to unsupervised learning.

It may be understood that, the target object may be an object of any type and any granularity in a character, an animal, a plant, an item, a portion, an organ, or a hyperplastic tissue that needs to be positioned and recognized from an image.

The hyperplastic tissue is a tissue that is not native but grows at a later stage.

In an embodiment, the hyperplastic tissue may be a hyperplastic tissue in a human body. In an embodiment, the hyperplastic tissue may include a colorectal polyp. It may be understood that, polyp refers to a neoplasm growing on a surface of a human tissue. In modern medicine, neoplasms growing on a surface of a human mucosa are collectively referred to as polyps. The colorectal polyp is a neoplasm growing on a surface of a colon or rectum.

In the object detection model training method in the embodiments of the disclosure, a living target object is not directly acted in the real world, but an image including a target object is acquired as a sample image for model training. This belongs to a combination of an image processing technology for ML training.

It may be understood that, the computer device needs to train the object detection model through a plurality of rounds of iterations. Therefore, this round is a current round of ML training. It may be understood that, in each round of iterative training, model parameters of the initial detection model of the current round are adjusted to make the model to gradually converge to obtain a final object detection model. Therefore, the initial detection model is a detection model before the model parameters are not adjusted in the round of training.

Specifically, the computer device may directly obtain a first sample image. The computer device may alternatively obtain a video stream, separate frames including images from the video stream, and use each image as a first sample image. The computer device may input the first sample image into the initial detection model of the current round, and predict a target object in the first sample image by using the initial detection model, to obtain a first prediction result for the target object.

The first prediction result is a result of predicting the target object in the first sample image. The first prediction result may include a position prediction result for the target object. That is, the first prediction result includes a first prediction position region of the target object. The first prediction position region is a predicted position region in which the target object in the first sample image is located.

It may be understood that, there may be a plurality of first prediction position regions in each first sample image. When there are the plurality of first prediction position regions, it indicates that the initial detection model outputs a plurality of position regions in which the target object may exist, that is, the first prediction position regions. In other embodiments, there may alternatively be one first prediction position region. The initial detection model selects, according to first class probabilities corresponding to position regions from the predicted position regions in which the target object may exist, a position region in which the target object is most likely to be located, that is, the first prediction position region. This is not limited.

In an embodiment, the first prediction result may further include first class probabilities corresponding to first prediction position regions, in addition to the first prediction position regions including the target object. The first class probability, that is, a classification probability, is used for representing a probability that the object located in each first prediction position region separately belongs to each preset class.

S204. Transform the first sample image and a first prediction position region of the target object in the first prediction result to obtain a second sample image and a prediction transformation result for the target object in the second sample image.

It may be understood that, the second sample image is a sample image obtained by transforming the first sample image. The prediction transformation result is obtained by transforming the first prediction position region, and is used for representing the target object in a second sample image. That is, the prediction transformation result may position the target object in the second sample image.

In an embodiment, the prediction transformation result may include a transformed position region. The transformed position region is a position region obtained by transforming the first prediction position region.

After the first prediction position region is transformed, the obtained transformed position region can still be used for identifying image content identified in the first sample image before the transformation.

Specifically, when the first sample image and the first prediction position region are transformed, the first prediction position region may be regarded as a part of the first sample image for whole transformation. For example, if the image content of the first sample image needs to be flipped horizontally, the first prediction position region in the first sample image regarded as a part of the first sample image also needs to be flipped horizontally together. That is, it is impossible to perform completely irrelevant or even opposite transformation on the first sample image and the first prediction position region, because a prediction transformation result after such transformation has no reference. For example, if the image content of the first sample image is flipped horizontally, but the first prediction position region is not flipped horizontally or the first prediction position region is flipped vertically, a transformed first prediction position region is completely unable to identify the content identified before the transformation.

In an embodiment, for each first sample image, the computer device may transform all the first prediction position regions in the first sample image. In other embodiments, the computer device may alternatively obtain a part of the first prediction position regions through screening from the first prediction position regions, and perform whole transformation on the first sample image and the obtained first prediction position regions through screening.

It may be understood that, the computer device may perform data augmentation processing on the first sample image and the first prediction position region to transform the first sample image and the first prediction position region.

In an embodiment, the computer device may transform the first sample image and the first prediction position region by using at least one data augmentation processing including color perturbation, horizontal flipping, image stretching and translation, and an affine change.

FIG. 3 is a schematic diagram of data augmentation in an embodiment. Referring to any group in FIG. 3(a) to FIG. 3(d), a left image in each group of images is a first sample image before transformation, and a right image is a transformed second sample image through used data augmentation processing. For example, in (a), color perturbation is performed on the left image (the first sample image) to obtain the right image (the second sample image). A box in the left image is used for representing a first prediction position region, a box in the right image is a transformed position region, and a prediction transformation result may be obtained according to the transformed position region. It can be learned from FIG. 3 that according to any data augmentation processing result in (a) to (d), a transformed position region can still identify image content identified in the first sample image before the transformation.

In an embodiment, when a first prediction result includes a first class probability, the prediction transformation result may alternatively include the first class probability. It may be understood that, after being transformed, the first prediction position region can still be used for identifying the image content identified in the first sample image before the transformation. Therefore, a class probability corresponding to the transformed position region is not transformed, and is still a first class probability corresponding to the first prediction position region before the transformation.

S206. Input the second sample image into the initial detection model, and output a second prediction result for the target object.

Specifically, the computer device may input the transformed second sample image into the initial detection model again to predict the target object in the second sample image to obtain a second prediction result for the target object.

The second prediction result is a result of predicting the target object in the second sample image. The second prediction result may include a position prediction result for the target object. That is, the second prediction result includes a second prediction position region of the target object. The second prediction position region is a predicted position region in which the target object in the second sample image is located.

In an embodiment, the second prediction result may further include second class probabilities corresponding to second prediction position regions, in addition to the second prediction position regions including the target object. The second class probability, that is, a classification probability, is used for representing a probability that the object located in each second prediction position region separately belongs to each preset class.

S208. Obtain a loss value of unsupervised learning according to a difference between the second prediction result and the prediction transformation result.

Specifically, the computer device may use the prediction transformation result as supervision information to supervise the second prediction result, and calculate a loss to obtain a loss of unsupervised learning.

It may be understood that, because the first sample image does not carry position annotation information of the target object, the first sample image belongs to unannotated sample data. Although the second sample image has a corresponding prediction transformation result, the second sample image is not manually annotated. Therefore, the prediction transformation result is used as supervision information, to supervise the second prediction result, and a loss is calculated, which belongs to a process of unsupervised learning. Therefore, a loss of the unsupervised learning is obtained.

If positioning of the target object, that is, the first prediction position region of the target object in the first sample image, can be obtained in forward prediction of the initial detection model, when the first sample image and the first prediction position region are transformed, and the transformed second sample image is inputted into the initial detection model again for secondary forward prediction, a position of the target object may be obtained. In this case, if the prediction transformation result obtained by transforming the first prediction position region before is a known result before the secondary forward prediction, the result may be used as supervision information (that is, a true value), to supervise the result of the secondary forward prediction (that is, the second prediction result), and a difference is calculated to obtain a loss value of unsupervised learning. That is, the loss value of the unsupervised learning is obtained by constraining consistency between the two prediction results.

In an embodiment, the second prediction result includes a second prediction position region of the target object and a corresponding second class probability; and the prediction transformation result includes a transformed position region of the target object and a corresponding first class probability. It may be understood that, for a difference between the second prediction result and the prediction transformation result, the difference may be calculated from at least one dimension of position consistency and classification consistency, thereby calculating a consistency constraint loss, and obtaining a loss value of unsupervised learning.

S210. Adjust model parameters of the initial detection model according to the total loss value.

It may be understood that, if a training end condition is not met, a next round is used as a current round, and the operation S202 of inputting a first sample image into an initial detection model of a current round is returned to perform iterative training. If the training end condition is met, the iterative training is stopped to obtain an object detection model.

The training end condition is a condition for ending the training.

In an embodiment, the training end condition may include that the model reaches a convergence state. In other embodiments, the training end condition may further include that a quantity of iteration times reaches a preset quantity threshold.

In an embodiment, the computer device may adjust model parameters of the initial detection model according to only the loss value of the unsupervised learning. That is, the computer device may train an object detection model through only the unsupervised learning. Specifically, the computer device may determine, according to the loss value of the unsupervised learning, whether the detection model obtained after the model parameters are adjusted converges, and if yes, use the detection model as the object detection model. It may be understood that in other embodiments, when it is determined according to the loss value that the model does not reach the convergence state, but the quantity of iteration times reaches the preset quantity threshold, the detection model of the current round obtained after the model parameters are adjusted may alternatively be used as a final object detection model.

It may be understood that, the computer device may alternatively use the unsupervised learning as one training branch, and combine with a supervised learning branch, to implement semi-supervised learning (SSL), to obtain an object detection model. In this case, the computer device may then perform supervised learning training on the initial detection model according to a part of the sample images carrying position annotation information of the target object, to obtain a loss value of supervised learning; and further adjust model parameters of the initial detection model according to the loss value of the unsupervised learning and the loss value of the supervised learning.

Semi-supervised learning (SSL): It performs mode recognition by using a large amount of unannotated data and annotated data together. When the SSL is used, as few workers as possible are required to work, and relatively high accuracy can be achieved.

In the foregoing object detection model training method, an unannotated first sample image is inputted into an initial detection model of a current round, and a first prediction result for a target object is outputted; further, the first sample image and a first prediction position region of the target object in the first prediction result are transformed, to obtain a second sample image and a prediction transformation result for the target object in the second sample image; the second sample image is inputted into the initial detection model, and a second prediction result for the target object is outputted; the prediction transformation result is used as supervision information to supervise the second prediction result, to determine a difference between the second prediction result and the prediction transformation result, so as to obtain a loss value of unsupervised learning; and model parameters of the initial detection model are adjusted according to the loss value to perform iterative training. That is, the transformed image is predicted again, and a second prediction result that is predicted again is supervised based on a transformed prediction transformation result as supervision information, to calculate an unsupervised loss, so that an object detection model is trained according to the unannotated sample data, and a cost is saved compared with that of a conventional requirement of a large amount of annotated data.

In an embodiment, the first prediction result includes the first prediction position region of the target object and a first class probability corresponding to the first prediction position region. In this embodiment, operation S204 includes: transforming the first sample image and the first prediction position region to obtain the second sample image and a transformed position region of the target object in the second sample image; and obtaining the prediction transformation result for the target object in the second sample image according to the transformed position region and the corresponding first class probability, the transformed position region corresponding to the first class probability corresponding to the first prediction position region before transformation.

The transformed position region is a position region obtained by transforming the first prediction position region. It may be understood that, because the first sample image and the first prediction position region in the first sample image are used as a whole for transformation, and the second sample image is obtained by transforming the first sample image, the transformed position region can identify the target object in the second sample image.

It may be understood that, after being transformed, the first prediction position region can still be used for identifying the image content identified in the first sample image before the transformation. Therefore, a class probability corresponding to the transformed position region is not transformed, and is still a first class probability corresponding to the first prediction position region before the transformation. Therefore, the transformed position region corresponds to the first class probability corresponding to the first prediction position region before the transformation. Further, the computer device may use the transformed position region and the corresponding first class probability as a prediction transformation result for the target object in the second sample image.

In an embodiment, for each first sample image, the computer device may obtain a part of first prediction position regions in the first sample image through screening for transformation to obtain transformed position regions. For example, the computer device may obtain a part of first prediction position regions through screening according to confidence levels of the first prediction position regions to perform transformation. The obtained first prediction position regions through screening have higher confidence levels than first prediction position regions that are not obtained through screening.

In an embodiment, the transforming the first sample image and the first prediction position region to obtain the second sample image and a transformed position region of the target object in the second sample image includes: obtaining a confidence level of the first prediction position region; obtaining a target prediction position region through screening from the first prediction position region according to the confidence level, a confidence level of the target prediction position region being greater than a confidence level of a non-prediction position region in the first prediction position region; and transforming the first sample image and the target prediction position region to obtain the second sample image and the transformed position region of the target object in the second sample image.

The confidence level is used for representing a credibility level at which an object in the first prediction position region is the target object. The target prediction position region is a first prediction position region that has a high confidence level and is used for transformation.

In an embodiment, the computer device may select, from the first prediction position regions, a preset quantity of first prediction position regions with confidence levels ranked top as target prediction position regions. The preset quantity is one or more.

For ease of understanding, description is made by using an example. If 4 first prediction position regions are predicted in a first sample image A, first prediction position regions with first 2 confidence levels may be selected as target prediction position regions according to confidence levels of the first prediction position regions, and whole transformation may be further performed on the first sample image A and the 2 target prediction position regions, to obtain a second sample image A' and 2 transformed position regions in the second sample image A'.

In an embodiment, the transforming the first sample image and the target prediction position region to obtain a second sample image and a transformed position region of the target object in the second sample image includes: decoding the target prediction position region, to generate a prediction box used for identifying the target object; and transforming the first sample image and the prediction box in the first sample image to obtain the second sample image and a transformed prediction box in the second sample image, the transformed prediction box being used for identifying the transformed position region of the target object in the second sample image.

The transformed prediction box is a box obtained by transforming the prediction box. The prediction box is a predicted frame used for identifying the target object. Decoding refers to a processing process of presenting the position region as a box.

It may be understood that, the prediction result may be converted into a box level through decoding, so that it is more convenient to transform the prediction result at the box level.

For example, if 4 first prediction position regions are predicted in a first sample image A, first prediction position regions with first 2 confidence levels may be selected as target prediction position regions according to confidence levels of the first prediction position regions. Further, the 2 target prediction position regions may be decoded to obtain 2 prediction boxes. Then, whole transformation may be performed on the first sample image A and the 2 prediction boxes, to obtain a second sample image A' and 2 transformed prediction boxes in the second sample image A'.

It may be understood that, in the foregoing embodiment, predicted first prediction position regions are first obtained through screening, and the target prediction position regions obtained through screening are then decoded to form a prediction transformation result at a box level. The prediction transformation result includes a relatively reliable prediction box. It may be understood that, if the first prediction result includes a first class probability, the prediction transformation result may include a relatively credible prediction box (that is, a prediction box with a high confidence level) and a corresponding first class probability.

In other embodiments, the first prediction position regions may alternatively be first decoded into prediction boxes, target prediction boxes with high confidence levels are then selected from the prediction boxes according to confidence levels of the prediction boxes, and the first sample image and the target prediction boxes in the first sample image are further transformed to obtain a second sample image and transformed prediction boxes in the second sample image.

Specifically, in an embodiment, the transforming the first sample image and the first prediction position regions to obtain a second sample image and transformed position regions of the target object in the second sample image may include: decoding the first prediction position regions of the target object to generate prediction boxes used for identifying the target object; obtaining confidence levels of the prediction boxes, and selecting target prediction boxes from the prediction boxes according to the confidence levels, confidence levels of the target prediction boxes being greater than confidence levels of non-target prediction boxes in the prediction boxes; and transforming the first sample image and the target prediction boxes in the first sample image to obtain the second sample image and transformed prediction boxes in the second sample image, The transformed prediction box is a box obtained by transforming the prediction box. The prediction box is a predicted frame used for identifying the target object. The confidence level of the prediction box is used for representing a credibility level at which an object in the prediction box is the target object.

Specifically, the computer device decodes the first prediction position region in which the target object is predicted, to generate a prediction box used for identifying the target object. It may be understood that, each prediction box has a corresponding confidence level. The computer device may select a target prediction box from the prediction boxes according to the confidence levels of the prediction boxes, the confidence level of the target prediction box being greater than confidence levels of non-target prediction boxes in the prediction boxes.

In an embodiment, the computer device may select, from the prediction boxes, a preset quantity of prediction boxes with confidence levels ranked top as target prediction boxes. The preset quantity is one or more.

Further, the computer device may transform the first sample image and the target prediction box in the first sample image to obtain the second sample image and a transformed prediction box in the second sample image.

For ease of understanding, description is made by using an example. If 4 prediction boxes are predicted in a first sample image A, prediction boxes with first 2 confidence levels may be selected as target prediction boxes according to confidence levels of the prediction boxes, and whole transformation may be further performed on the first sample image A and the 2 target prediction boxes to obtain a second sample image A' and 2 transformed prediction boxes in the second sample image A'.

In an embodiment, the loss value is a first loss value. The method further includes: performing supervised learning on the initial detection model according to a third sample image to obtain a second loss value of a current round of supervised learning. In this embodiment of the disclosure, the operation S210 of adjusting model parameters of the initial detection model according to the loss value includes: adjusting the model parameters of the initial detection model according to the first loss value and the second loss value.

The third sample image carries position annotation information of the target object. That is, the third sample image is sample data with annotation.

The supervised learning, that is, fully supervised learning (FSL): It performs mode recognition by using only annotated data. Because the third sample image carries the position annotation information of the target object, supervised learning training may be performed on the initial detection model of the current round according to the third sample image carrying the position annotation information of the target object to obtain a second loss value of a current round of supervised learning.

The computer device may determine a total loss value of the current round of the initial detection model according to the first loss value and the second loss value. Further, the computer device may adjust model parameters of the initial detection model according to the total loss value and a gradient descent algorithm.

In an embodiment, the adjusting the model parameters of the initial detection model according to the first loss value and the second loss value includes: obtaining a first loss weight of the unsupervised learning and a second loss weight of the supervised learning; performing weighted average processing on the first loss value according to the first loss weight and the second loss value according to the second loss weight to obtain a total loss value of the current round of the initial detection model; and adjusting the model parameters of the initial detection model according to the total loss value.

It may be understood that, magnitudes of the first loss weight and the second loss weight determine an unsupervised learning result and a supervised learning result, and a degree of impact on the training of the initial detection model. The first loss weight may be greater than, less than, or equal to the second loss weight. This is not limited.

In the foregoing embodiment, the unsupervised loss is combined with the supervised loss to implement SSL training, thereby improving the accuracy of the model training.

In an embodiment, a model training framework of the initial detection model includes a feature extraction backbone, a prediction backbone, and an unsupervised learning branch. The inputting a first sample image into an initial detection model of a current round, and outputting a first prediction result for a target object includes: inputting the first sample image into the feature extraction backbone to extract an image feature of the first sample image; and inputting the image feature of the first sample image into the prediction backbone to predict the first prediction result for the target object. In this embodiment, the transforming the first sample image and a first prediction position region of the target object in the first prediction result includes: transforming the first sample image and the first prediction position region of the target object in the first prediction result in the unsupervised learning branch.

The model training framework is a neural network architecture used for training an object detection model. It may be understood that, model training frameworks corresponding to different rounds of initial detection models remain unchanged.

The feature extraction backbone is a backbone structure used for performing feature extraction on an image. The prediction backbone is a backbone structure for predicting a target object based on an extracted image feature. The unsupervised learning branch is a branch structure for unsupervised learning training.

It may be understood that, the backbone structure is a structure that shares processing functions. That is, the backbone structure may further help other branches complete shared processing, in addition to helping the unsupervised learning branch complete the shared processing. For example, the feature extraction backbone may further help other branches complete feature extraction related processing, in addition to helping the unsupervised learning branch complete feature extraction processing. The branch is a structure that does not share processing and is used for special processing. For example, the unsupervised learning branch is a structure that specializes in processing unsupervised learning.

Specifically, a model training framework of the initial detection model includes a feature extraction backbone, a prediction backbone, and an unsupervised branch. During the current round of the unsupervised learning training, the computer device may input the first sample image into the feature extraction backbone, to extract an image feature of the first sample image; and input the image feature of the first sample image into the prediction backbone, to predict the first prediction result for the target object. In this embodiment, the transforming the first sample image and a first prediction position region of the target object in the first prediction result includes: transforming the first sample image and the first prediction position region of the target object in the first prediction result in the unsupervised learning branch.

The unsupervised branch only exists during model training. Therefore, when the model training is completed, a trained feature extraction backbone and prediction backbone are reserved in a finally obtained object detection model to position and recognize a target object in a target image to be processed.

In an embodiment, the initial detection model further includes a supervised learning branch. In this embodiment, the performing supervised learning on the initial detection model according to a third sample image to obtain a second loss value of a current round of supervised learning includes: inputting the third sample image into the feature extraction backbone to obtain an image feature of the third sample image; inputting the image feature of the third sample image into the prediction backbone to obtain a prediction result for the target object in the third sample image; and in the supervised learning branch, determining the second loss value of the current round of supervised learning according to a difference between the prediction result and the position annotation information of the target object.

The supervised learning branch is a branch structure for supervised (fully supervised) learning training.

It may be understood that, the supervised learning branch and the unsupervised learning branch share the feature extraction backbone and the prediction backbone to extract image features and predict target objects.

Specifically, the computer device may input the third sample image into the feature extraction backbone to obtain an image feature of the third sample image. The computer device may input the image feature of the third sample image extracted by the feature extraction backbone into the prediction backbone to obtain a prediction result for the target object in the third sample image; and in the supervised learning branch, determine the second loss value of the current round of supervised learning according to a difference between the prediction result and the position annotation information of the target object carried in the third sample image.

For ease of understanding, the principle of the model training is explained and described with reference to FIG. 4. An example in which the target object is a colorectal polyp is used in FIG. 4. Referring to FIG. 4, initial sample data is annotated data (that is, a third sample image carrying position annotation information of a target object) and unannotated data (that is, a first sample image not carrying position annotation information of a target object). In FIG. 4, to increase a quantity of samples of the unannotated data, data augmentation is performed on the unannotated data. It may be understood that in other embodiments, if there are enough unannotated data, the processing operation of performing data augmentation on the unannotated data may alternatively be omitted. It may be understood that, a branch formed by the unannotated data is an unsupervised learning branch (see a solid-line box 402), and a branch formed by the annotated data is a supervised learning branch (see a dashed-line box 404). It can be learned from FIG. 4 that the unsupervised learning branch 402 and the supervised learning branch 404 share a feature extraction backbone and a prediction backbone.

For the unsupervised learning branch 402, a first prediction result for a target object in a first sample image is predicted by using the feature extraction backbone and the prediction backbone. The first prediction result includes first prediction position regions and corresponding first class probabilities. Next, the first prediction position region is obtained through screening and is decoded to display a prediction result at a box level, that is, to obtain a prediction box through decoding. Then, data augmentation is performed on the first sample image and the prediction box to obtain the second sample image and a transformed prediction box. A candidate box 406a in FIG. 4 is the prediction box of a first sample image 406, and the first sample image 406 and the candidate box 406a are flipped horizontally, to obtain a second sample image 408 and a transformed prediction box 408a (that is, candidate box information after data augmentation identified in the figure). Further, a prediction transformation result for the target object in the second sample image is obtained according to the transformed prediction box and a corresponding first class probability. Next, the second sample image after data augmentation is then inputted into the initial detection model again (that is, the feature extraction backbone and the prediction backbone), and a second prediction result for the target object is outputted. Then, the prediction transformation result is used as supervision information, to supervise the second prediction result, and a loss is calculated, to obtain an unsupervised loss (that is, a first loss value of unsupervised learning).

For supervised learning branch 404, a prediction result for the target object in the third sample image is predicted by using the feature extraction backbone and the prediction backbone. A fully supervised loss (that is, a second loss value of FSL) is obtained according to a difference between the prediction result and the position annotation information of the target object carried in the third sample image (that is, annotation box information in FIG. 4). Further, a network may be optimized and updated according to the first loss value and the second loss value. That is, model parameters of the initial detection model of the current round are optimized and updated.

In the foregoing embodiment, by sharing the feature extraction backbone and the prediction backbone, the model training framework can be simplified, and system resources can be saved. In addition, feature extraction and a prediction part of training of the unsupervised learning and the supervised learning can also be unified for training, instead of using respective independent branches for training, but for joint training, thereby improving the accuracy of the model training.

In an embodiment, the second prediction result includes a second prediction position region of the target object and a corresponding second class probability; and the prediction transformation result includes a transformed position region of the target object and a corresponding first class probability. In this embodiment, the obtaining a loss value of unsupervised learning according to a difference between the second prediction result and the prediction transformation result includes: recognizing, according to the second class probability, the second prediction position region belonging to a foreground region and the second prediction position region belonging to a background region; for the second prediction position region belonging to the foreground region, obtaining a foreground loss value according to a difference between the second class probability corresponding to the second prediction position region and the first class probability corresponding to the transformed position region; for the second prediction position region belonging to the background region, calculating a cross-entropy loss for the second class probability corresponding to the second prediction position region to obtain a background loss value; and performing weighted average processing on the foreground loss value according to a foreground weight and the background loss value according to a background weight, to obtain the loss value of the unsupervised learning, the foreground weight being greater than the background weight.

The foreground loss value is a difference loss between a prediction result for the foreground region in the second prediction result and the prediction transformation result. The background loss value is a difference loss between a prediction result for the background region in the second prediction result and the prediction transformation result. The foreground weight is a weight of the foreground loss value, and is used for representing a degree of impact of the foreground loss value on the model training. The background weight is a weight of the background loss value, and is used for representing a degree of impact of the background loss value on the model training.

In this embodiment, for a difference between the second prediction result and the prediction transformation result, the difference may be calculated from a dimension of classification consistency, thereby calculating a consistency constraint loss and obtaining a loss value of unsupervised learning.

It may be understood that, the second prediction position region included in the second prediction result may include a foreground region and a background region. The foreground region is a region in which the target object is located. The background region is a region in the image other than the foreground region.

In this case, the computer device may recognize, according to the second class probability, the second prediction position region belonging to a foreground region and the second prediction position region belonging to a background region; for the second prediction position region belonging to the foreground region, the computer device may obtain a foreground loss value according to a difference between the second class probability corresponding to the second prediction position region and the first class probability corresponding to the transformed position region.

In addition, for the second prediction position region belonging to the background region, because the second prediction position region has no information that may play a supervisory role, the computer device may calculate a cross-entropy loss for the second class probability corresponding to the second prediction position region belonging to the background region, to obtain a background loss value.

Further, the computer device may obtain a foreground weight and a background weight. The computer device may perform weighted average processing on the foreground loss value according to a foreground weight and the background loss value according to a background weight, to obtain the loss value of the unsupervised learning, the foreground weight being greater than the background weight.

In an embodiment, the computer device may determine a loss value of unsupervised learning according to the following formula:

i.

$$L_{cl} = \lambda^+ \sum_{a \in A+} L_{cl}^+(p_{\tilde{x}_u}^a, p_{x_u}) + \lambda^- \sum_{a \in A-} L_{cl}^-(p_{\tilde{x}_u}^a),$$

the foregoing formula representing a consistency constraint loss function of the unsupervised learning; $L_{cl}$ being a loss of unsupervised learning; $L_{cl}$ a subscript cl in $L_{cl}$ representing consistency loss calculation from a dimension of classification consistency; $\lambda^+$ being a foreground weight; $a \in A+$ being an $a^{th}$ foreground region belonging to a foreground region set A+ (that is, an $a^{th}$ second prediction position region belonging to the foreground region); $L_{cl}^+(p_{\tilde{x}_u}^a, p_{x_u})$ being a foreground loss; $p_{\tilde{x}_u}^a$ being a second class probability of the predicted $a^{th}$ foreground region; $p_{x_u}$ being a first class probability corresponding to the transformed position region (that is, serving as supervision information, and equivalent to a true value); $\lambda^-$ being a background weight, $L_{cl}^-(p_{\tilde{x}_u}^a)$ being a background loss; $a \in A-$ being an $a^{th}$ background region belonging to a background region set A- (that is, an $a^{th}$ second prediction position region belonging to the background region); and $p_{\tilde{x}_u}^a$ in $L_{cl}^-(p_{\tilde{x}_u}^a)$ representing a second class probability of the predicted $a^{th}$ background region.

It may be understood that, if the second prediction position region is represented as a prediction box, that is, is in the form of a box level, the foreground region in the foregoing formula is a foreground box, and the background region is a background box. The foreground box is a box in which an identified object is a target object. The background box is a box in which an identified object is a non-target object.

Specifically, the computer device may directly obtain a preset foreground weight and background weight, or may combine a quantity of foreground regions and background regions to determine a foreground weight and a background weight.

It may be understood that, for a general image, a background region is often far greater than a foreground region, and the foreground region includes most of useful information for detecting the target object. Therefore, to make the consistency constraint better pay attention to the foreground region, the foreground weight may be greater than the background weight.

In an embodiment, the foreground weight may be a ratio of a quantity of second prediction position regions belonging to the background region to a total quantity of second prediction position regions. The background weight may be a ratio of a quantity of second prediction position regions belonging to the foreground region to the total quantity of second prediction position regions.

In an embodiment, a foreground weight and a background weight may be determined according to the following formulas:

i.

$$\lambda^+ = \frac{N^-}{N}; \text{ and } \lambda^- = \frac{N^+}{N},$$

$\lambda^+$ being the foreground weight, $\lambda^-$ being the background weight, $N^-$ being the quantity of background regions, $N^+$ being the quantity of foreground regions, and N being the total quantity of second prediction position regions.

Because the quantity of background regions is relatively large, corresponding ratios are exchanged, that is, the ratio of the background region is used as the foreground weight, and the ratio of the foreground region is used as the background weight. In this way, the foreground weight may be greater than the background weight, the foreground weight and the background weight may be further dynamically determined according to an actual situation, and compared with a preset fixed weight, the accuracy is improved.

Figure 5:
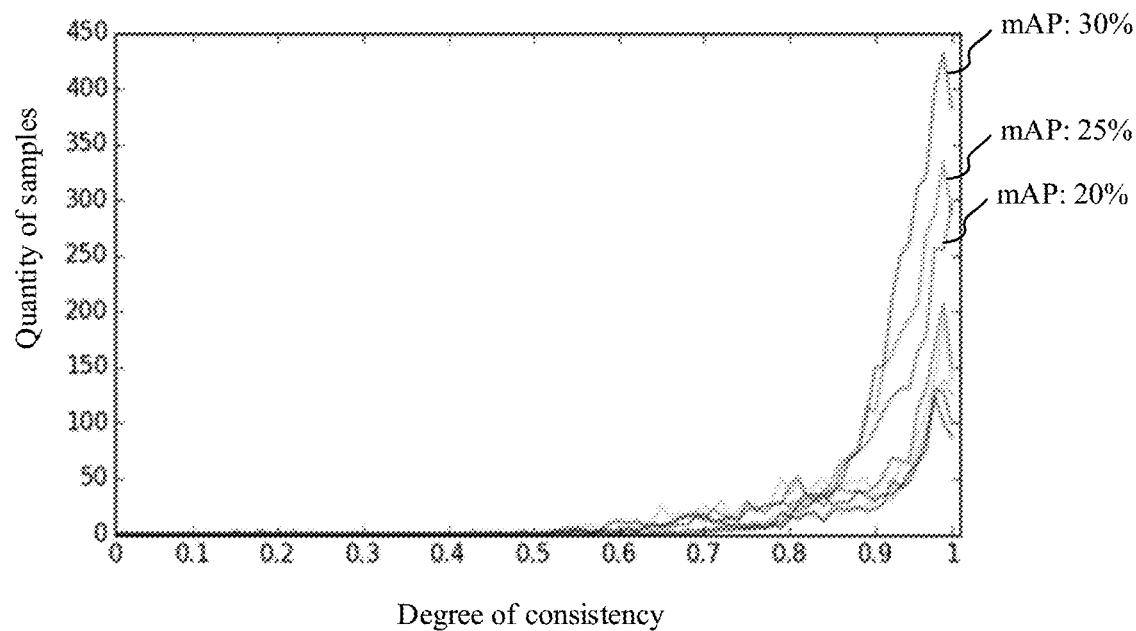
FIG. 5 is a schematic diagram of a statistical result of position consistency in an embodiment.
Figure 6:
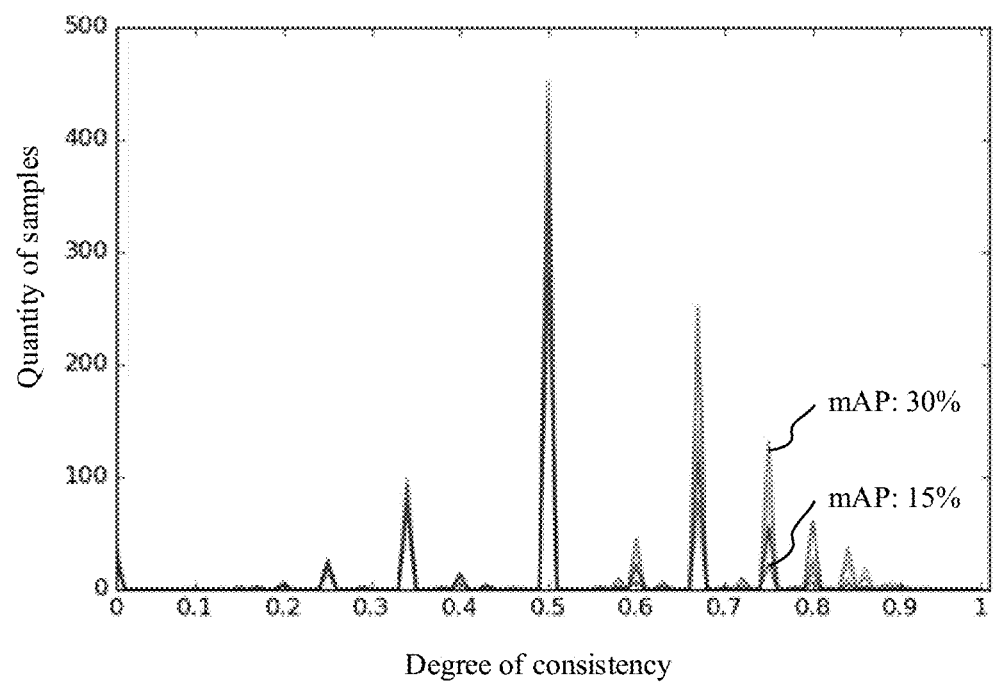
FIG. 6 is a schematic diagram of a statistical result of classification consistency in an embodiment.

It may be understood that, in an object detection algorithm, a classification dimension is used for determining class labels of prediction boxes, including class labels of a background and an included object, and a position regression dimension is used for fine-tuning positions of the prediction boxes. Similarly, in the consistency constraint, the classification dimension is used for constraining a determining consistency between classes of prediction boxes at a same position, and the position regression dimension is used for constraining a consistent fine-tuning direction of the prediction boxes at the same position. A large amount of pairs of data before and after transformation is tested by using the object detection algorithm, to obtain statistical results of an experiment under a detector on samples at different mean average precision (where mAP is an important indicator for measuring accuracy of the object detection algorithm in DL, higher mAP indicates better detection performance, and a range is 0-100%) shown in FIG. 5 and FIG. 6. In FIG. 5 and FIG. 6, different curves represent test results of the detector at different mAP degrees. For example, curves of mAP 30%, mAP 25%, and mAP 20% are identified in FIG. 5 are respectively test statistical results under the detector at mAP 30%, mAP 25%, and mAP 20% degrees. In another example, curves of mAP 30% and mAP 15% identified in FIG. 6 are respectively test statistical results of under the detector at mAP 30% and mAP 15% degrees. Curves under all mAP degrees in FIG. 5 and FIG. 6 are not identified, and only a part is identified for illustration. FIG. 5 shows a statistical result of position consistency (that is, from a dimension of position consistency, a statistical consistency loss). Referring to FIG. 5, a horizontal axis represents a degree of consistency (0 to 1), and a vertical axis represents a quantity of statistical samples. It can be learned from FIG. 5 that regardless of the mAP degrees, a degree of consistency between most samples reaches 80% or even more than 90%, and a difference between positions is basically indistinguishable by naked eyes. For example, in terms of mAP 30% and mAP 25%, under the two mAP degrees, a degree of consistency between most samples is more than 90%. Therefore, the position consistency loss is generally relatively small, and fails in playing an important role in constraining model convergence training. FIG. 6 shows a statistical result of classification consistency (that is, from a dimension of classification consistency, a statistical consistency loss). A horizontal axis represents a degree of consistency (0 to 1), and a vertical axis represents a quantity of statistical samples. It can be learned from FIG. 6 that distribution of the classification consistency is different, and a degree of consistency between most samples is concentrated at 0.5. That is, higher consistency is not achieved between more samples. Therefore, when the model does not converge, the classification consistency loss is relatively large, and it is more meaningful to establish the consistency constraint on the dimension of the classification consistency, which has a relatively important impact on the model convergence. Therefore, in the foregoing embodiment of the disclosure, the consistency constraint loss is calculated from the dimension of the classification consistency, to obtain a loss value of unsupervised learning.

In an embodiment, the first sample image is an initial colorectal polyp sample image; the target object is a colorectal polyp; the second sample image is obtained by transforming the colorectal polyp sample image; and the object detection model is a colorectal polyp detection model.

It may be understood that, property recognition of the colorectal polyp in an endoscopic video stream is an important application of AI medical assistance, and aims to help doctors find polyps in time and guide the doctors perform a next operation of determining and operation during endoscopic examination. Colorectal polyp positioning detection is an extremely important and critical part of a whole procedure of the property recognition of the colorectal polyp in the endoscopic video stream.

In this embodiment of the disclosure, an initial unannotated colorectal polyp sample image may be used as the first sample image in each embodiment of the disclosure, and the colorectal polyp may be used as the target object in each embodiment of the disclosure for unsupervised training, to obtain a colorectal polyp detection model through training. Therefore, the colorectal polyp positioning detection is implemented according to unannotated data, thereby saving manual annotation costs.

It may be understood that in other embodiments, some annotated colorectal polyp sample images may alternatively be used for supervised learning, and a loss of supervised learning is combined with a loss of unsupervised learning, to implement SSL, so that an accurate colorectal polyp detection model can be trained with less annotated data.

In an embodiment, the method further includes: obtaining a target colorectal polyp medical image to be processed; inputting the target colorectal polyp medical image into the colorectal polyp detection model, to predict a positioning result of the colorectal polyp; and identifying a colorectal polyp region in the target colorectal polyp medical image according to the positioning result.

Specifically, the computer device may input a target colorectal polyp medical image into the colorectal polyp detection model trained in the method according to the embodiments of the disclosure to predict a positioning result of a colorectal polyp. Further, the computer device may identify a colorectal polyp region in the target colorectal polyp medical image according to the positioning result, to remind a medical worker of a specific position of the polyp. It may be understood that, the identified colorectal polyp region may provide input data for a next operation of property recognition of the polyp.

In an embodiment, the computer device may obtain a target colorectal polyp medical image from the medical image video stream (for example, an endoscopic video stream), and each target colorectal polyp medical image is a video frame. The computer device may position and identify a colorectal polyp region for each frame of target colorectal polyp medical image.

In the foregoing embodiment, the colorectal polyp detection model trained in the embodiments of the disclosure may accurately position and detect the colorectal polyp to provide an accurate and important reference basis for subsequent medical treatment.

It may be understood that in other embodiments, for positioning and detection of another medical detection object (such as a uterine polyp or a tumor) that needs to be positioned and detection in the medical field, each medical detection object to be deleted may be used as the target object in each embodiment of the disclosure, a medical image including the object is used as a sample image, and an object detection model for detecting the object is obtained by using the model training method in the embodiments of the disclosure. That is, the object detection model training method in the embodiments of the disclosure is applicable to more medical detection scenarios, and is not limited to the positioning and detection of the colorectal polyp.

In addition, the object detection model training method in the embodiments of the disclosure is further applicable to other scenarios than the medical detection scenario, such as a face recognition scenario, a game object detection scenario, and a vehicle recognition scenario.

It may be understood that in other embodiments, the computer device may also perform supervised training according to some annotated sample images to obtain a preliminary detection model, then predict unannotated sample images by using the preliminary detection model, and automatically annotate the sample images according to predicted position regions. Then, the computer device puts the annotated sample images and the sample images annotated by using the preliminary detection model together as whole annotated sample images for model training, until the model converges to obtain a final object detection model. This is another manner of implementing semi-supervised training.

In an embodiment, an object detection method is provided, and is performed by a computer device. In the object detection method, a target image to be processed may be inputted into the object detection model trained in the method according to the embodiments of the disclosure, and a positioning result for a target object in the target image is outputted.

It may be understood that, for the object detection method in the embodiments of the disclosure, an object detection apparatus may be correspondingly provided, to implement the foregoing object detection method.

In an embodiment, an object detection method is provided, and is performed by a computer device. The computer device may be one or more devices. For example, the computer device may be a server or a terminal, or may be a combination of a server and a terminal. That is, the object detection method may be performed by the server, or may be implemented by the terminal and the server together. The method includes: inputting a target colorectal polyp medical image to be processed into a pre-trained colorectal polyp detection model to predict a positioning result of a colorectal polyp.

In this embodiment, training operations of the colorectal polyp detection model include: inputting an unannotated first colorectal polyp sample medical image into an initial detection model of a current round, and outputting a first prediction result for a colorectal polyp; transforming the first colorectal polyp sample medical image and a first prediction position region of the colorectal polyp in the first prediction result to obtain a second colorectal polyp sample medical image and a prediction transformation result for the colorectal polyp in the second colorectal polyp sample medical image; inputting the second colorectal polyp sample medical image into the initial detection model, and outputting a second prediction result for the colorectal polyp; obtaining a loss value of unsupervised learning according to a difference between the second prediction result and the prediction transformation result; and adjusting model parameters of the initial detection model according to the loss value, using a next round as the current round, and returning to the operation of inputting a first colorectal polyp sample medical image into an initial detection model of a current round to perform iterative training, until a training end condition is met, to obtain a colorectal polyp detection model.

In the foregoing embodiment, the colorectal polyp detection model with higher accuracy can be trained with the unannotated data, which not only saves manual annotation costs, but also accurately positions and detects the colorectal polyp to provide an accurate and important reference basis for subsequent medical treatment.

Figure 7:
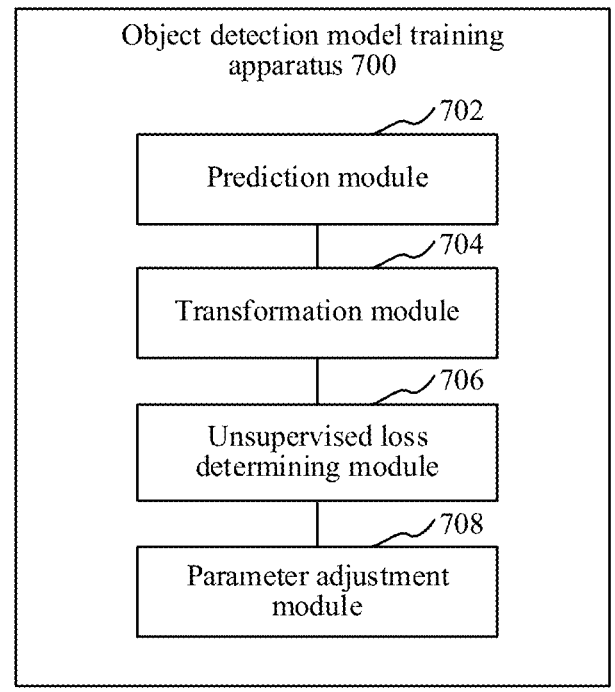
FIG. 7 is a block diagram of an object detection model training apparatus in an embodiment.

As shown in FIG. 7, in an embodiment, an object detection model training apparatus 700 is provided, and is disposed in the computer device in the foregoing embodiments. The apparatus 700 includes: a prediction module 702, a transformation module 704, an unsupervised loss determining module 706, and a parameter adjustment module 708.

The prediction module 702 is configured to input a first sample image into an initial detection model of a current round and output a first prediction result for a target object, the first sample image not carrying position annotation information of the target object.

The transformation module 704 is configured to transform the first sample image and a first prediction position region of the target object in the first prediction result to obtain a second sample image and a prediction transformation result for the target object in the second sample image.

The prediction module 702 is further configured to input the second sample image into the initial detection model and output a second prediction result for the target object.

The unsupervised loss determining module 706 is configured to obtain a loss value of unsupervised learning according to a difference between the second prediction result and the prediction transformation result.

The parameter adjustment module 708 is configured to adjust model parameters of the initial detection model according to the loss value, notify the prediction module 702 to use a next round as the current round, and continue to perform the operation of inputting a first sample image into an initial detection model of a current round to perform iterative training, until a training end condition is met to obtain an object detection model.

In an embodiment, the first prediction result includes the first prediction position region of the target object and a first class probability corresponding to the first prediction position region; and the transformation module 704 is further configured to transform the first sample image and the first prediction position region to obtain the second sample image and a transformed position region of the target object in the second sample image; and obtain the prediction transformation result for the target object in the second sample image according to the transformed position region and the corresponding first class probability, the transformed position region being corresponding to the first class probability corresponding to the first prediction position region before transformation.

In an embodiment, the transformation module 704 is further configured to obtain a confidence level of the first prediction position region; obtain a target prediction position region through screening from the first prediction position region according to the confidence level, a confidence level of the target prediction position region being greater than a confidence level of a non-prediction position region in the first prediction position region; and transform the first sample image and the target prediction position region to obtain the second sample image and the transformed position region of the target object in the second sample image.

In an embodiment, the transformed position region is a transformed prediction box; and the transformation module 704 is further configured to decode the target prediction position region, to generate a prediction box used for identifying the target object; and transform the first sample image and the prediction box in the first sample image, to obtain the second sample image and a transformed prediction box in the second sample image.

In an embodiment, the loss value is a first loss value. The apparatus 700 further includes:

a supervised loss determining module 707, configured to perform supervised learning on the initial detection model according to a third sample image, to obtain a second loss value of a current round of supervised learning, the third sample image carrying the position annotation information of the target object.

The parameter adjustment module 708 is further configured to adjust the model parameters of the initial detection model according to the first loss value and the second loss value.

In an embodiment, a model training framework of the initial detection model includes a feature extraction backbone, a prediction backbone, and an unsupervised learning branch.

The prediction module 702 is further configured to input the first sample image into the feature extraction backbone to extract an image feature of the first sample image; and input the image feature of the first sample image into the prediction backbone to predict the first prediction result for the target object; and the transformation module 704 is further configured to, in the unsupervised learning branch, transform the first sample image and the first prediction position region of the target object in the first prediction result.

In an embodiment, the model training framework further includes a supervised learning branch.

The prediction module 702 is further configured to input the third sample image into the feature extraction backbone, to obtain an image feature of the third sample image; and input the image feature of the third sample image into the prediction backbone, to obtain a prediction result for the target object in the third sample image; and the supervised loss determining module 707 is further configured to, in the supervised learning branch, determine the second loss value of the current round of supervised learning according to a difference between the prediction result and the position annotation information of the target object.

In an embodiment, the parameter adjustment module 708 is further configured to obtain a first loss weight of the unsupervised learning and a second loss weight of the supervised learning; perform weighted average processing on the first loss value according to the first loss weight and the second loss value according to the second loss weight to obtain a total loss value of the current round of the initial detection model; and adjust the model parameters of the initial detection model according to the total loss value.

In an embodiment, the second prediction result includes a second prediction position region of the target object and a corresponding second class probability; and the prediction transformation result includes a transformed position region of the target object and a corresponding first class probability. The unsupervised loss determining module 706 is further configured to recognize, according to the second class probability, the second prediction position region belonging to a foreground region and the second prediction position region belonging to a background region; for the second prediction position region belonging to the foreground region, obtain a foreground loss value according to a difference between the second class probability corresponding to the second prediction position region and the first class probability corresponding to the transformed position region; for the second prediction position region belonging to the background region, calculate a cross-entropy loss for the second class probability corresponding to the second prediction position region, to obtain a background loss value; and perform weighted average processing on the foreground loss value according to a foreground weight and the background loss value according to a background weight, to obtain the loss value of the unsupervised learning, the foreground weight being greater than the background weight.

In an embodiment, the first sample image is an initial colorectal polyp sample image; the target object is a colorectal polyp; the second sample image is obtained by transforming the colorectal polyp sample image; and the object detection model is a colorectal polyp detection model.

Figure 8:
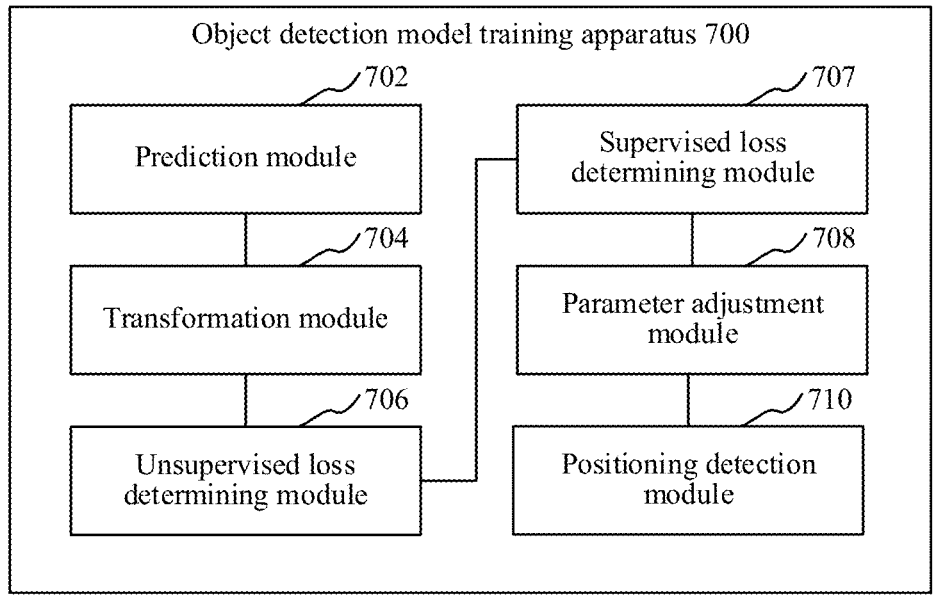
FIG. 8 is a block diagram of an object detection model training apparatus in another embodiment.

As shown in FIG. 8, in an embodiment, the apparatus 700 further includes: a supervised loss determining module 707 and a positioning detection module 710.

The positioning detection module 710 is configured to obtain a target colorectal polyp medical image to be processed; input the target colorectal polyp medical image into the colorectal polyp detection model to predict a positioning result of the colorectal polyp; and identify a colorectal polyp region in the target colorectal polyp medical image according to the positioning result.

Figure 9:
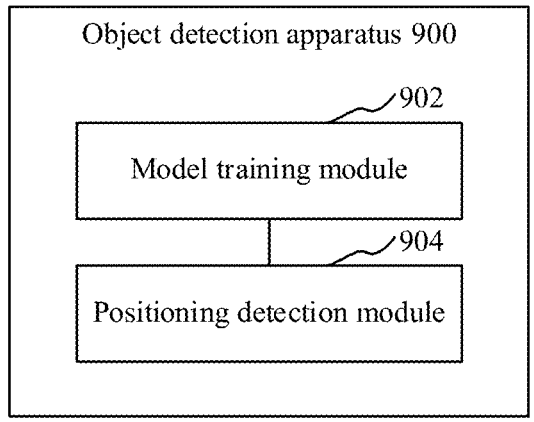
FIG. 9 is a block diagram of an object detection apparatus in an embodiment.

As shown in FIG. 9, in an embodiment, an object detection apparatus 900 is provided, and is disposed in the computer device in the foregoing embodiments. The apparatus 900 includes: a model training module 902 and a positioning detection module 904.

The model training module 902 is configured to input an unannotated first colorectal polyp sample medical image into an initial detection model of a current round, and output a first prediction result for a colorectal polyp; transform the first colorectal polyp sample medical image and a first prediction position region of the colorectal polyp in the first prediction result, to obtain a second colorectal polyp sample medical image and a prediction transformation result for the colorectal polyp in the second colorectal polyp sample medical image; input the second colorectal polyp sample medical image into the initial detection model, and output a second prediction result for the colorectal polyp; obtain a loss value of unsupervised learning according to a difference between the second prediction result and the prediction transformation result; and adjust model parameters of the initial detection model according to the loss value, use a next round as the current round, and return to the operation of inputting a first colorectal polyp sample medical image into an initial detection model of a current round to perform iterative training, until a training end condition is met, to obtain a colorectal polyp detection model.

The positioning detection module 904 inputs a target colorectal polyp medical image to be processed into a pre-trained colorectal polyp detection model to predict a positioning result of a colorectal polyp.

The model training module 902 in this embodiment of the disclosure may perform the operations in the object detection model training method described in the embodiments of the disclosure to obtain a colorectal polyp detection model through training.

For either a specific limitation on the object detection model training apparatus or the object detection apparatus, refer to the limitation on the object detection model training method or the object detection method above. Details are not described herein again. The modules, or code, in the foregoing object detection model training apparatus or the foregoing object detection apparatus may be implemented entirely or partially through software, hardware, or a combination thereof. The modules may be embedded into or independent of a processor of a computer device in a hardware form, or may be stored in a memory of the computer device in a software form, so that the processor invokes and performs the operations corresponding to the modules.

Figure 10:
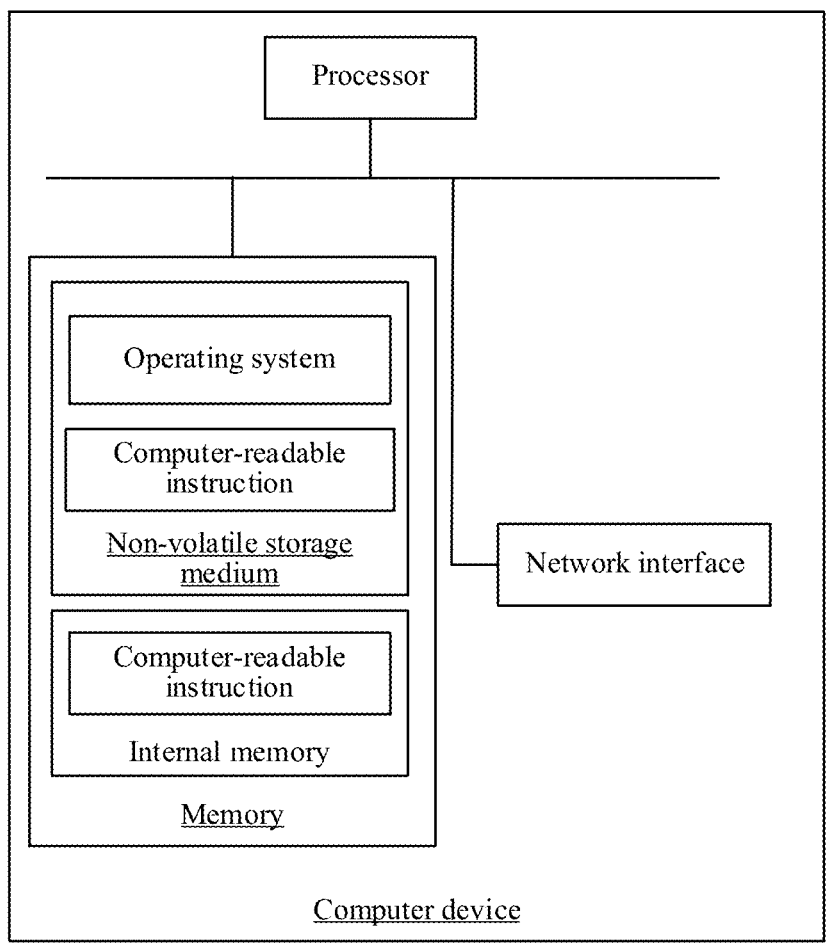
FIG. 10 is a block diagram of a computer device in an embodiment.

FIG. 10 is a block diagram of a computer device in an embodiment. Referring to FIG. 10, the computer device may be a terminal or a server. The computer device includes one or more processors, a memory, and a network interface that are connected by using a system bus. The memory includes a non-volatile storage medium and an internal memory. The non-volatile storage medium of the computer device may store an operating system and computer-readable instructions. When executed, the computer-readable instructions may cause the one or more processors to perform the object detection model training method or the object detection method. The one or more processors of the computer device are configured to provide calculation and control capabilities, to support running of the entire computer device. The internal memory may store computer-readable instructions. When executed by the one or more processors, the computer-readable instructions may cause the one or more processors to perform the object detection model training method or the object detection method. The network interface of the computer device is configured to perform network communication.

A person skilled in the art may understand that, the structure shown in FIG. 10 is only a block diagram of a part of a structure related to a solution of the disclosure and does not limit the computer device to which the solution of the disclosure is applicable. Specifically, the computer device may include more or fewer members than those in the drawings, or some components are combined, or a different component deployment is used.

In an embodiment, the object detection model training apparatus or the object detection apparatus provided in the disclosure may be implemented in the form of computer-readable instructions. The computer-readable instructions may be run on the computer device shown in FIG. 10, and the non-volatile storage medium of the computer device may store program modules or code constituting the object detection model training apparatus and the object detection apparatus, for example, the prediction module 702, the transformation module 704, the unsupervised loss determining module 706, and the parameter adjustment module 708 shown in FIG. 7. The computer-readable instructions constituted by the program modules are configured for causing the computer device to perform the operations in the object detection model training method or the object detection method in the embodiments of the disclosure. In some embodiments, modules (and other equivalent terms such as units) may be implemented using hardware such as a processor and/or memory. A combination of software and hardware is also contemplated.

For example, the computer device may input a first sample image into an initial detection model of a current round by using the prediction module 702 in the object detection model training apparatus 700 shown in FIG. 7, and output a first prediction result for a target object; the first sample image not carrying position annotation information of the target object. The computer device may transform the first sample image and a first prediction position region of the target object in the first prediction result by using the transformation module 704 to obtain a second sample image and a prediction transformation result for the target object in the second sample image. The computer device may input, by using the prediction module 702 the second sample image into the initial detection model, and output a second prediction result for the target object. The computer device may obtain a loss value of unsupervised learning according to a difference between the second prediction result and the prediction transformation result by using the unsupervised loss determining module 706. The computer device may adjust, by using the parameter adjustment module 708, model parameters of the initial detection model according to the loss value, notify the prediction module 702 to use a next round as the current round, and continue to perform the operation of inputting a first sample image into an initial detection model of a current round to perform iterative training, until a training end condition is met, to obtain an object detection model.

In an embodiment, a computer device is provided, including a memory and one or more processors, the memory storing computer-readable instructions, the computer-readable instructions, when executed by the one or more processors, causing the one or more processors to perform the operations in the foregoing object detection model training method. Herein, the operations in the object detection model training method may be the operations of the object detection model training method in the foregoing embodiments.

In an embodiment, one or more computer-readable storage media are provided, storing computer-readable instructions, the computer-readable instructions, when executed by one or more processors, causing the one or more processors to perform the operations in the foregoing object detection model training method. Herein, the operations in the object detection model training method may be the operations of the object detection model training method in the foregoing embodiments.

It is to be understood that although the operations in the embodiments of the disclosure are not necessarily performed sequentially in a sequence indicated by operation numbers. Unless clearly specified in this specification, there is no strict sequence limitation on the execution of the operations, and the operations may be performed in another sequence. Moreover, at least some of the operations in each embodiment may include a plurality of sub-operations or a plurality of stages. The sub-operations or stages are not necessarily performed at the same moment but may be performed at different moments. The sub-operations or stages are not necessarily performed sequentially, but may be performed in turn or alternately with another operation or at least some of sub-operations or stages of the another operation.

A person of ordinary skill in the art may understand that all or some procedures in the method in the foregoing embodiments may be implemented by a computer-readable instruction instructing relevant hardware. The program may be stored in a non-volatile computer-readable storage medium. When the program is executed, the procedures of the foregoing method embodiments may be implemented. Any reference to a memory, a storage, a database, or another medium used in the embodiments provided in the disclosure may include a non-volatile and/or volatile memory. The non-volatile memory may include a read-only memory (ROM), a programmable ROM (PROM), an electrically programmable ROM (EPROM), an electrically erasable programmable ROM (EEPROM), a flash memory, or the like. The volatile memory may include a random access memory (RAM) or an external cache. As an illustration instead of a limitation, the RAM is available in various forms, such as a static RAM (SRAM), a dynamic RAM (DRAM), a synchronous DRAM (SDRAM), a double data rate SDRAM (DDRSDRAM), an enhanced SDRAM (ESDRAM), a synchronization link (Synchlink) DRAM (SLDRAM), a rambus direct RAM (RDRAM), a direct rambus dynamic RAM (DRDRAM), and a rambus dynamic RAM (RDRAM).

The technical features in the foregoing embodiments may be combined in different manners. For concise description, not all possible combinations of the technical features in the embodiments are described. However, combinations of the technical features are considered as falling within the scope described in this specification provided that the combinations of the technical features do not conflict with each other.

The foregoing embodiments only describe several implementations of the disclosure, which are described specifically and in detail, but cannot be construed as a limitation to the patent scope of the disclosure. For a person of ordinary skill in the art, several transformations and improvements can be made without departing from the idea of the disclosure. These transformations and improvements belong to the protection scope of the disclosure. Therefore, the protection scope of the patent of the disclosure is subject to the appended claims.

What is claimed is:

1. An object detection model training method, performed by a computer device, the method comprising:
    inputting a first sample image into an initial detection model of a current round, and outputting a first prediction result for a target object, the first prediction result including a first prediction position region of the target object corresponding to a predicted position of the target object in the first sample image, the first sample image not carrying position annotation information of the target object;
    transforming the first sample image and the first prediction position region of the target object in the first prediction result to obtain a second sample image and a prediction transformation result for the target object in the second sample image;
    inputting the second sample image into the initial detection model, and outputting a second prediction result for the target object;
    obtaining a loss value of unsupervised learning according to a difference between the second prediction result and the prediction transformation result; and
    adjusting model parameters of the initial detection model according to the loss value, using a next round as the current round, and returning to the operation of inputting a first sample image into an initial detection model of a current round to perform iterative training until a training end condition is met, to obtain an object detection model.

2. The object detection model training method according to claim 1, wherein the first prediction result comprises the first prediction position region of the target object and a first class probability corresponding to the first prediction position region; and
    the transforming comprises:
    transforming the first sample image and the first prediction position region to obtain the second sample image and a transformed position region of the target object in the second sample image; and
    obtaining the prediction transformation result for the target object in the second sample image according to the transformed position region and the corresponding first class probability, the transformed position region being corresponding to the first class probability corresponding to the first prediction position region before transformation.

3. The object detection model training method according to claim 2, wherein the transforming the first sample image and the first prediction position region to obtain the second sample image and a transformed position region of the target object in the second sample image comprises:
    obtaining a confidence level of the first prediction position region;
    obtaining a target prediction position region through screening from the first prediction position region according to the confidence level, a confidence level of the target prediction position region being greater than a confidence level of a non-prediction position region in the first prediction position region; and
    transforming the first sample image and the target prediction position region to obtain the second sample image and the transformed position region of the target object in the second sample image.

4. The object detection model training according to claim 3, wherein the transforming the first sample image and the target prediction position region to obtain a second sample image and a transformed position region of the target object in the second sample image comprises:
    decoding the target prediction position region, to generate a prediction box used for identifying the target object; and
    transforming the first sample image and the prediction box in the first sample image to obtain the second sample image and a transformed prediction box in the second sample image, the transformed prediction box being used for identifying the transformed position region.

5. The object detection model training method according to claim 4, wherein the adjusting comprises:
    obtaining a first loss weight of the unsupervised learning and a second loss weight of the supervised learning;
    performing weighted average processing on the first loss value according to the first loss weight and the second loss value according to the second loss weight to obtain a total loss value of the current round of the initial detection model; and
    adjusting the model parameters of the initial detection model according to the total loss value.

6. The object detection model training method according to claim 1, wherein the loss value of the unsupervised learning is a first loss value; the method further comprises:

performing supervised learning on the initial detection model according to a third sample image to obtain a second loss value of a current round of supervised learning, the third sample image carrying the position annotation information of the target object; and the adjusting comprises:

adjusting the model parameters of the initial detection model according to the first loss value and the second loss value.

7. The object detection model training method according to claim 5, wherein a model training framework of the initial detection model comprises a feature extraction backbone, a prediction backbone, and an unsupervised learning branch;

the inputting a first sample image into an initial detection model of a current round, and outputting a first prediction result for a target object comprises:

inputting the first sample image into the feature extraction backbone to extract an image feature of the first sample image; and inputting the image feature of the first sample image into the prediction backbone to predict the first prediction result for the target object; and the transforming the first sample image and a first prediction position region of the target object in the first prediction result comprises:

in the unsupervised learning branch, transforming the first sample image and the first prediction position region of the target object in the first prediction result.

8. The object detection model training method according to claim 7, wherein the model training framework further comprises a supervised learning branch;

the performing supervised learning on the initial detection model according to a third sample image to obtain a second loss value of a current round of supervised learning comprises:

inputting the third sample image into the feature extraction backbone, to obtain an image feature of the third sample image;

inputting the image feature of the third sample image into the prediction backbone, to obtain a prediction result for the target object in the third sample image; and in the supervised learning branch, determining the second loss value of the current round of supervised learning according to a difference between the prediction result and the position annotation information of the target object.

9. The object detection model training method according to claim 1, wherein the second prediction result comprises a second prediction position region of the target object and a corresponding second class probability; the prediction transformation result comprises a transformed position region of the target object and a corresponding first class probability; and the obtaining comprises:

recognizing the second prediction position region belonging to a foreground region and the second prediction position region belonging to a background region according to the second class probability;

for the second prediction position region belonging to the foreground region, obtaining a foreground loss value according to a difference between the second class probability corresponding to the second prediction position region and the first class probability corresponding to the transformed position region;

for the second prediction position region belonging to the background region, calculating a cross-entropy loss for the second class probability corresponding to the second prediction position region to obtain a background loss value; and performing weighted average processing on the foreground loss value according to a foreground weight and the background loss value according to a background weight to obtain the loss value of the unsupervised learning, the foreground weight being greater than the background weight.

10. The object detection model training method according to claim 1, wherein the first sample image is an initial colorectal polyp sample image;

the target object is a colorectal polyp; the second sample image is obtained by transforming the colorectal polyp sample image; and the object detection model is a colorectal polyp detection model.

11. The object detection model training method according to claim 10, further comprising:

obtaining a target colorectal polyp medical image to be processed;

inputting the target colorectal polyp medical image into the colorectal polyp detection model to predict a positioning result of the colorectal polyp; and identifying a colorectal polyp region in the target colorectal polyp medical image according to the positioning result.

12. An object detection model training apparatus, comprising:

at least one memory configured to store program code;

at least one processor configured to read the program code and operate as instructed by the program code, the program code comprising:

prediction code configured to cause the at least one processor to input a first sample image into an initial detection model of a current round, and output a first prediction result for a target object, the first prediction result including a first prediction position region of the target object corresponding to a predicted position of the target object in the first sample image, the first sample image not carrying position annotation information of the target object;

transformation code configured to cause the at least one processor to transform the first sample image and the first prediction position region of the target object in the first prediction result, to obtain a second sample image and a prediction transformation result for the target object in the second sample image, the prediction code being further configured to cause the at least one processor to input the second sample image into the initial detection model, and output a second prediction result for the target object;

unsupervised loss determining code configured to cause the at least one processor to obtain a loss value of unsupervised learning according to a difference between the second prediction result and the prediction transformation result; and parameter adjustment code configured to cause the at least one processor to adjust model parameters of the initial detection model according to the loss value, notify the prediction module to use a next round as the current round, and continue to perform the operation of inputting a first sample image into an initial detection model of a current round to perform iterative training until a training end condition is met, to obtain an object detection model.

13. The object detection model training apparatus according to claim 12, wherein the first prediction result comprises the first prediction position region of the target object and a first class probability corresponding to the first prediction position region; and the transformation code is further configured to cause the at least one processor to:
transform the first sample image and the first prediction position region to obtain the second sample image and a transformed position region of the target object in the second sample image; and
obtain the prediction transformation result for the target object in the second sample image according to the transformed position region and the corresponding first class probability, the transformed position region being corresponding to the first class probability corresponding to the first prediction position region before transformation.

14. The object detection model training apparatus according to claim 13, wherein the transformation code is further configured to cause the at least one processor to:
obtain a confidence level of the first prediction position region;
obtain a target prediction position region through screening from the first prediction position region according to the confidence level, a confidence level of the target prediction position region being greater than a confidence level of a non-prediction position region in the first prediction position region; and
transform the first sample image and the target prediction position region to obtain the second sample image and the transformed position region of the target object in the second sample image.

15. The object detection model training apparatus according to claim 14, wherein the transformation code is configured to cause the at least one processor to:
decode the target prediction position region to generate a prediction box used for identifying the target object; and
transform the first sample image and the prediction box in the first sample image to obtain the second sample image and a transformed prediction box in the second sample image, the transformed prediction box being used for identifying the transformed position region.

16. The object detection model training apparatus according to claim 15, wherein the parameter adjustment code is further configured to cause the at least one processor to:
obtain a first loss weight of the unsupervised learning and a second loss weight of the supervised learning;
perform weighted average processing on the first loss value according to the first loss weight and the second loss value according to the second loss weight to obtain a total loss value of the current round of the initial detection model; and
adjust the model parameters of the initial detection model according to the total loss value.

17. The object detection model training apparatus according to claim 12, wherein the loss value of the unsupervised learning is a first loss value; the program code further comprises:
supervised loss determining code configured to cause the at least one processor to perform supervised learning on the initial detection model according to a third sample image to obtain a second loss value of a current round of supervised learning, the third sample image carrying the position annotation information of the target object; and the parameter adjustment code is further configured to cause the at least one processor to:
adjust the model parameters of the initial detection model according to the first loss value and the second loss value.

18. The object detection model training apparatus according to claim 17, wherein a model training framework of the initial detection model comprises a feature extraction backbone, a prediction backbone, and an unsupervised learning branch;
the prediction code is further configured to cause the at least one processor to:
input the first sample image into the feature extraction backbone to extract an image feature of the first sample image; and
input the image feature of the first sample image into the prediction backbone to predict the first prediction result for the target object; and
the transformation code is further configured to cause the at least one processor to:
in the unsupervised learning branch, transform the first sample image and the first prediction position region of the target object in the first prediction result.

19. The object detection model training apparatus according to claim 18, wherein the model training framework further comprises a supervised learning branch;
the prediction code is further configured to cause the at least one processor to:
input the third sample image into the feature extraction backbone to obtain an image feature of the third sample image;
input the image feature of the third sample image into the prediction backbone to obtain a prediction result for the target object in the third sample image; and
the supervised loss determining code is further configured to cause the at least one processor to, in the supervised learning branch, determine the second loss value of the current round of supervised learning according to a difference between the prediction result and the position annotation information of the target object.

20. A non-transitory computer-readable storage medium, storing computer program code that when executed by at least one processor causes the at least one processor to:
input a first sample image into an initial detection model of a current round, and outputting a first prediction result for a target object, the first prediction result including a first prediction position region of the target object corresponding to a predicted position of the target object in the first sample image, the first sample image not carrying position annotation information of the target object;
transform the first sample image and a first prediction position region of the target object in the first prediction result to obtain a second sample image and a prediction transformation result for the target object in the second sample image;
input the second sample image into the initial detection model, and output a second prediction result for the target object;
obtain a loss value of unsupervised learning according to a difference between the second prediction result and the prediction transformation result; and
adjust model parameters of the initial detection model according to the loss value, using a next round as the current round, and return to the operation of inputting a first sample image into an initial detection model of a current round to perform iterative training until a training end condition is met, to obtain an object detection model.

\* \* \* \* \*